(12) United States Patent
Yonan et al.

(10) Patent No.: US 7,575,858 B2
(45) Date of Patent: Aug. 18, 2009

(54) METHOD OF VISUALIZING PROTEINS BOUND TO PROTEIN-BINDING MEMBRANES

(75) Inventors: Christopher R. Yonan, Plymouth Meeting, PA (US); Frank N. Chang, Dresher, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 230 days.

(21) Appl. No.: 10/525,168

(22) PCT Filed: Sep. 9, 2003

(86) PCT No.: PCT/US03/28478
§ 371 (c)(1),
(2), (4) Date: Feb. 22, 2005

(87) PCT Pub. No.: WO2004/025253
PCT Pub. Date: Mar. 25, 2004

(65) Prior Publication Data
US 2005/0214735 A1    Sep. 29, 2005

Related U.S. Application Data

(60) Provisional application No. 60/409,857, filed on Sep. 11, 2002.

(51) Int. Cl.
*C12Q 1/00* (2006.01)
(52) U.S. Cl. .................................................. 435/4
(58) Field of Classification Search .................. 435/4, 435/180; 436/531, 86, 532
See application file for complete search history.

(56) References Cited

U.S. PATENT DOCUMENTS

| | | | |
|---|---|---|---|
| 3,873,426 A * | 3/1975 | Katchalski et al. | 435/176 |
| 4,247,401 A | 1/1981 | Bloch et al. | 210/638 |
| 4,431,546 A | 2/1984 | Hughes et al. | 210/656 |
| 4,500,321 A | 2/1985 | Hugelshofer et al. | 8/527 |
| 5,508,177 A | 4/1996 | Dotzlaf et al. | 435/70.1 |
| 5,795,759 A | 8/1998 | Rosazza et al. | 435/189 |
| 6,174,729 B1 * | 1/2001 | Alam | 436/86 |
| 6,319,720 B1 | 11/2001 | Wondrak | 436/86 |
| 2003/0228621 A1 * | 12/2003 | Qin et al. | 435/7.1 |

FOREIGN PATENT DOCUMENTS

GB    2 053 926 A    2/1981

OTHER PUBLICATIONS

Miyagi, Y. "Applicability of Coomassie Brilliant Blue . . . " Seibutsu Butsuri Kagaku (1975) 19(2): 129-137 (abstract only); downloaded from Caplus database on STN on Aug. 27, 2007.*
Prinout from Registry Database on STN for RN 70788-63-5; downloaded on Aug. 27, 2007.*
Hopwood et al. (1973) "An investigation of the chlorotriazine . . . " Histochemical J. (1973) 5: 391-403.*
Bayramoglu et al. "Procion Brown MX-5BR . . . " Chem. Engineer. Sci. (Jul. 2002) 57: 2323-2334.*
"Iontosorb Brown" in "IONTOSORB— Bead Cellulose Derivatives", www.iontosorb.com (May 6, 2002).

* cited by examiner

*Primary Examiner*—Sandra Saucier
*Assistant Examiner*—Susan Hanley
(74) *Attorney, Agent, or Firm*—Daniel A. Monaco; Drinker Biddle & Reath LLP

(57) ABSTRACT

A method of visualizing proteins bound to a protein-binding membrane is provided herein, comprising reacting proteins bound to protein-binding membranes with a compound of formula (I) wherein $R^a$, $R^1$, $R^2$, $R^3$, $R^4$, M, n, and m are as defined herein.

(I)

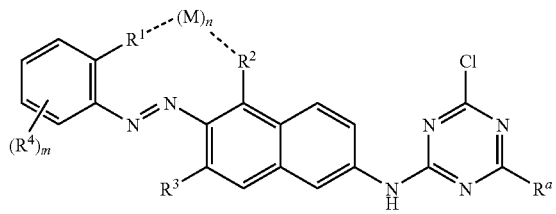

4 Claims, 4 Drawing Sheets

METHOD OF VISUALIZING PROTEINS BOUND TO PROTEIN-BINDING MEMBRANES

FIELD OF THE INVENTION

The present invention relates to the detection/visualization of proteins bound to a protein-binding membrane using staining reagents defined herein.

BACKGROUND OF THE INVENTION

Protein analyses often begin with electrophoretic separation of a mixture of proteins. In a typical application, proteins migrate through a gel under the influence of an electric field. The rate of migration is dependent on the charge, size and shape of the protein. When the separation is complete, blots, on protein-binding membranes are made from the gels on which the electrophoretic separation is performed.

The general techniques for protein separation and for blotting onto a protein-binding membrane are well known (*Techniques in Molecular Microbiology*, J. Walker and W. Gaastre (Eds); G. Bers and D. Garfin, Bio Techniques, Vol. 3, No. 4, pp. 276-288 (1985)).

"Protein blotting" is a term that refers to the transfer of electrophoretically-resolved protein samples to a protein-binding membrane prior to analysis for the presence of protein by a detection procedure such as immunodetection. Currently, protein-binding membranes include three main compositions that are used for protein blotting: nitrocellulose, nylon and polyvinylidene difluoride (PVDF). Other protein-binding membranes are also available.

After the blotting process, the protein bound to the membrane is visualized via any of a variety of techniques such as for example selective dyeing, radioactive marking, fluorescence, and chemiluminescence.

In immunodetection, a blot is subjected to a general protein stain such as amido black 10b or ponceau S (Nakamura et al., *Anal. Biochem.* 148: 311-319, 1985), coomassie brilliant blue R-250 (Burnette, *Anal. Biochem.* 112: 195-203, 1981), India ink (Hancock and Tsang, *Anal. Biochem.* 133: 157-162, 1983) or colloidal gold (Moeremans et al., *Anal. Biochem.* 145: 315-321, 1985; Dunn, *Methods in Mol. Biol.* 112: 319-329, 1999). A separate blot is often then used for the detection of immunoreactive proteins. Side-by-side comparison of the two blots reveals the general location of the immunogens.

Of the general protein stains, amido black 10b, ponceau S and coomassie blue have the advantage of involving relatively quick procedures, requiring about 10-20 minutes operation time. However these stains are characterized by low sensitivity, having a detection limit of about 50-100 ng of protein. India ink has a sensitivity limit of about 50 ng of protein. Staining with India ink requires about four hours to complete. Colloidal gold stain has the highest sensitivity (about 2 nanograms on PVDF membranes). However incubation times of several hours are required for staining with colloidal gold.

Staining efficiency with the stains described above is dependent on membrane composition. In particular, nylon membranes are incompatible with these stains because reactivity of the membrane itself generates a high staining background (Pluskal et al., *Biotechniques*, 4: 272-282, 1986). In addition, amido black 10b and coomassie blue, though often used for their ease of removal, are not easily removed from PVDF membranes. High background levels of these dyes remain even after extensive washing steps. An additional membrane limitation is that nitrocellulose membranes cannot be used in some staining procedures because of incompatibility with high concentrations of organic solvents such as methanol.

In order to perform additional characterization of a protein following visualization, the protein should remain essentially intact, i.e., retain tertiary structure, characteristic antigenic activity, enzymatic activity, etc, through staining, destaining and stain removal processes. In particular, harsh conditions are required to apply and remove colloidal gold (Magi et al., *Methods in Mol. Biol.* 112:431-443, 1999). Such harsh conditions often degrade the analyte proteins and thus preclude additional characterization that requires retention of the intact tertiary protein structure.

Thus, in current practice, staining procedures for proteins often involve reagent profiles that are undesirable for reasons including: low sensitivity; lengthy incubation time; reagents that denature or otherwise degrade the analyte proteins precluding further characterization such as immunodetection; and incompatibility with certain protein-binding membrane compositions.

What is needed is a stain and a staining procedure which:

(a) is as rapid as ponceau S or amido black 10b staining, i.e., requiring less than ten minutes;

(b) employs a dye that is easily removed from the protein-binding membrane in destaining, leaving levels of background stain that do not interfere with protein detection;

(c) has a detection limit similar to that achieved by colloidal gold, i.e., capable of allowing detection of proteins down to the nanogram range;

(d) employs reagents and conditions that allow staining and destaining without denaturation of the analyte proteins, thus preserving the characteristic antigenic activity, enzymatic activity, etc.;

(e) is reversible under conditions which do not denature or otherwise degrade the protein analyte and thus preserve the protein's characteristic antigenic activity, enzymatic activity, etc.; and (f) is broadly applicable to different protein substrates and to different protein-binding membranes.

SUMMARY OF THE INVENTION

In one embodiment of the present invention there is provided a method of visualizing a protein bound to a protein-binding membrane, said method comprising:

(1) providing at least one protein bound to a protein-binding membrane;

(2) staining the protein with an effective amount of a staining reagent comprising at least one compound of formula I:

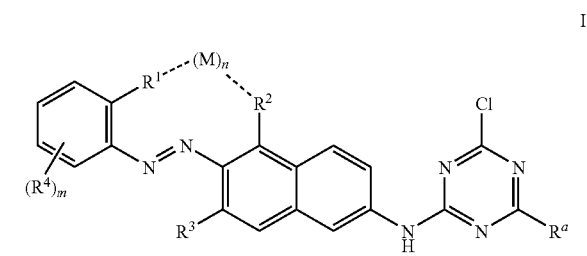

wherein, $R^a$ is selected from halogen and —NH—Ar;

$R^1$ and $R^3$ are independently selected from the group consisting of —OH, —COOH and —SO$_3$H;

$R^2$ is selected from the group consisting of —OH and —SH;

$R^4$ is selected from the group consisting of —COOH, —SO$_3$H, —NH$_2$, —NH(C$_1$-C$_6$)alkyl, —NHacyl, —NHAr, —OH and —O-acyl;

m is 0 or 1

M is a transition metal selected from the group consisting of chromium, manganese, iron, cobalt, nickel, copper, zinc, cadmium and combinations thereof;

n is 0 or 1;

- - - - - - indicates coordination to the transition metal M; and

Ar is unsubstituted phenyl or substituted phenyl;

wherein the substituents for Ar are selected from the group consisting halogen, —NO$_2$, and —SO$_3$H;

or a salt of such a compound;

(3) incubating said protein bound to the protein-binding membrane with said staining reagent for a time interval sufficient to allow reaction of the protein with the staining reagent to yield a stained protein;

(4) removing said staining reagent from the protein-binding membrane; and (5) observing the stained protein.

In one sub-embodiment of the invention, the protein is stained with a compound of formula I wherein:

$R^a$ is halogen;

$R^1$ is —COOH;

$R^2$ is —OH;

$R^3$ is —SO$_3$H;

m is 0;

M is chromium; and n is 0 or 1;

or a salt of such a compound.

In one embodiment of the invention the staining reagent is reactive brown 10.

The invention is also directed to a composition comprising at least one protein bound to a protein-binding membrane, which protein has been stained with a staining reagent comprising at least one compound of formula I. The protein may be applied to the protein-binding membrane by spotting a solution of the protein onto the membrane. Alternatively, the protein may be applied to the protein-binding membrane via a blot of an electrophoresis gel on which a separation of a mixture of proteins has been performed.

In another embodiment of the invention, there is provided a method of reversing a staining procedure as described above, comprising: (1) providing a protein-binding membrane having at least one protein spot bound thereto, stained with a staining reagent comprising at least one compound of formula I; (2) incubating said protein-binding membrane with an aqueous alkaline solution; and (3) washing the protein-binding membrane to remove the staining reagent.

The invention is also directed to a method of quantifying a protein analyte, comprising: (1) spotting the at least one protein analyte onto a protein-binding membrane to produce at least one protein analyte spot bound to the protein-binding membrane; (2) spotting a series of known concentrations of a protein standard onto the protein-binding membrane to produce a series of protein standard spots of known quantity bound to the protein-binding membrane; (3) staining the protein analyte spot and the protein standard spots with a staining reagent comprising at least one compound of formula I; (4) incubating the protein analyte spot and the protein standard spots bound to the protein-binding membrane with the staining reagent for a time interval sufficient to allow reaction of the protein spot and the protein standard spots with the staining reagent; (5) removing the staining reagent from the protein-binding membrane; (6) generating image quantification data for the protein standard spots and for the protein analyte spot; (7) constructing a standard calibration curve using the known concentrations of the protein standard and the corresponding image quantification data; and (8) calculating a concentration for the protein analyte.

The invention is also directed to a kit for visualizing a protein bound to a protein-binding membrane comprising: (1) one or more protein-binding membranes; and (2) a staining reagent comprising at least one compound of formula I.

In another embodiment of the invention, there is provided a kit for quantifying an amount of a protein, comprising: (1) one or more protein-binding membranes; (2) a staining reagent comprising at least one compound of formula I; and (3) a set of one or more solutions of a protein standards of known concentration.

Suitable protein standards useful in the kits described above for quantifying protein samples include, for example bovine serum albumin (BSA).

In certain preferred embodiments of the invention, the protein-binding membrane is selected from the group consisting of nitrocellulose, nylon and polyvinylidene difluoride (PVDF) membrane, and/or the staining reagent is reactive brown 10.

DETAILED DESCRIPTION OF THE INVENTION

Figure 1A:
FIGS. 1a-1e are photographic reproductions of PVDF membranes spotted with bovine serum albumin at six concentrations from 2 nanograms to 1 microgram and stained with: ponceau S (FIG. 1a); amido black 10b (FIG. 1b); coomassie blue (FIG. 1c); colloidal gold (FIG. 1d); and reactive brown 10 (FIG. 1e).

The present invention provides a method for visualizing a protein that is bound to a protein-binding membrane. The method is rapid and has a detection limit in the nanogram range. The method employs a dye reagent that is rapidly removed from most protein-binding membranes, leaving levels of background stain that do not interfere with protein detection. The method of the invention employs reagents and conditions for staining, destaining and reversal of the staining procedure, that do not denature or otherwise degrade protein analytes, but rather preserve any characteristic antigenic or enzymatic activity possessed by the protein. The method is broadly applicable to different proteins and to different compositions of protein-binding membranes.

Typically, proteins in a sample to be analyzed are separated using gel electrophoresis, or other types of electrophoresis.

The separated proteins are typically transferred from the electrophoresis gel to a protein-binding membrane. The staining methods of the present invention are particularly suited to detecting proteins separated by membrane electrophoresis, a technique that is the subject of the commonly owned U.S. Provisional Patent Application titled "System And Methods For Electrophoretic Separation Of Proteins On Protein Binding Membranes," Application Ser. No. 10/659,003, filed on even date herewith and incorporated herein by reference in its entirety.

Proteins may also be applied directly to a protein-binding membrane by spotting. Spotting of a protein on a membrane may be done by techniques known to those of skill in the art such as, for example using a capillary pipette to transfer a small amount of the protein dissolved in a solvent.

As used herein, "protein" refers to a molecule comprising at least two amino acid residues covalently linked by peptide bonds or modified peptide bonds (e.g., peptide isosteres). No limitation is placed on the maximum number of amino acids which may comprise a protein. The amino acids comprising the proteins referred to herein are may be D- or L-amino acids with, L-amino acids being preferred. In addition, the component amino acids may be β-amino acids, or custom synthesized amino acids or peptidomimetic fragments, e.g. a Friedinger γ lactam, a peptoid or the like, or mixtures of any of these substances. The terminology "a protein" is understood to cover a plurality of proteins, unless otherwise noted.

The proteins referred to herein may also be associated with one or more other molecules, including one or more other proteins, or with one or more metal atoms or metal complexes such as, for example a zinc finger protein. For example, a protein may comprise a homo- or heteromultimeric protein, an antibody/antigen complex, or a ligand/receptor complex. As used herein, the association of a protein with another protein or non-protein molecule is termed a "protein binding interaction." The proteins referred to herein may also exhibit biological activities, e.g., enzymatic, activities.

The proteins referred to herein may contain modifications. Such modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, labeling, either with radioactive or non-radioactive isotopes, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for example, *Proteins—Structure and Molecular Properties*, 2nd Ed., T. E. Creighton, W. H. Freeman and Company, New York, 1993; Wold F, Posttranslational Protein Modifications: Perspectives and Prospects, pgs. 1-12 in *Posttranslational Covalent Modification of Proteins*, B. C. Johnson, Ed., Academic Press, New York, 1983; Seifter et al., "Analysis for protein modifications and nonprotein cofactors," *Meth. Enzymol.* (1990) 182: 626-646; and Rattan et al. (1992), "Protein Synthesis: Posttranslational Modifications and Aging," *Ann NY Acad Sci* 663: 48-62, the entire disclosures of which are herein incorporated by reference.

The term "protein-binding membrane" refers to any solid immobilizing membrane matrix which is capable of binding protein molecules. Preferably, membranes for use in the present invention have a high protein binding capacity.

As used herein, a "high protein binding capacity" means membranes which bind, at room temperature, at least about 20 μg protein/cm$^2$ when the thickness of the membrane is about 0.15 mm. Preferably, the membranes used in the practice of the invention bind, at room temperature on a membrane of a thickness of about 0.15 mm, at least about 50 μg protein/cm$^2$, more preferably about 100 μg protein/cm$^2$ to about 250 μg protein/cm$^2$. Without wishing to be bound by any theory, it is believed that proteins bind to hydrophobic polymeric membranes via hydrophobic interactions, and bind to neutral hydrophilic membranes via ionic interactions.

Hydrophobic polymeric membranes and neutral or charged hydrophilic polymeric membranes that bind proteins can be used for the present invention. Examples of hydrophobic membranes comprise fluorinated polymers such as polyvinylidene difluoride (PVDF), polytetrafluoroethylene (PTFE); polyolefins such as polyethylene, polypropylene, polymethylpentene; polystyrenes; polysulfones; polyacrylates; polycarbonates; vinyl polymers such as polyvinyl chloride and polyacrylonitriles. Hydrophobic membranes can also comprise modified forms of the above polymers. For example, hydrophobic polymeric membranes can be modified to contain fixed formal positive charge groups by contacting the membranes with a polyamine or polyamido-polyamide epichlorohydrin resin. Preferably, the hydrophobic membranes comprise polymeric fluorocarbons such as polyvinylidene difluoride (PVDF).

Examples of neutral or charged polymeric membranes comprise polyamines such as nylons (e.g. nylon 66, nylon 6, nylon 610 or nylon 46); modified nylons (e.g. positively charged nylons), cellulose derivatives such as nitrocellulose, cellulose acetate, DEAE-cellulose; polyimides, polyesters; polyvinyl alcohols; polyvinylamines; polybenzylamines and polydiallylamines. Preferred hydrophilic membranes comprise nitrocellulose and neutral or positively charged nylons.

By "effective amount", with respect to the amount of dye used in staining a protein-binding membrane, is meant the amount of dye required to react with the protein bound to the protein-binding membrane to produce a visually detectable image of the protein spot bound to the membrane.

"Reactive brown 10" is a generic name for a dye compound of the following structure:

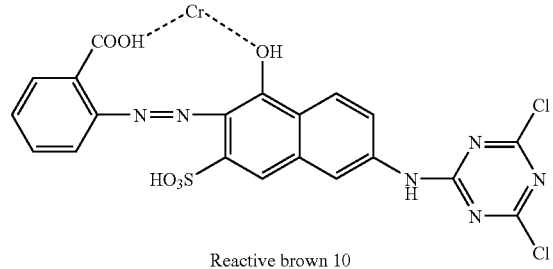

Reactive brown 10

The term "stain" used as a verb, or the term "staining," means the contacting of a staining reagent, comprising a compound such as a compound of formula I, with a protein-binding membrane containing one or more bound proteins.

The term "stain" used as a noun or the term "staining reagent" refers to chemical compounds, and compositions containing such compounds, which are capable of reacting with a substrate such as a protein to effect an observable color change in said substrate.

A "stained protein" means a protein bound to a protein-binding membrane which has been reacted with a staining reagent to effect a color change in the protein such that the protein is visually detectable.

The phrase "visualizing a protein" refers to any method whereby a protein spot on a protein-binding membrane is rendered visually detectable to the human eye via a color change that makes the protein spot visible.

The term "destain" or "destaining" means removing a stain such as a compound of formula I from the matrix of a protein-binding membrane while leaving the dye bound to the protein substrate thereon. Destaining is distinguished from reversal of the staining process, wherein the stain is removed from an analyte protein bound to a protein-binding membrane which has been previously stained, such that the analyte protein may be further analyzed via other methods, such as immunodetection.

The term "spot" or "spotting" refers to the application of a sample of an analyte protein to a protein-binding membrane.

The terms "blot" or "blotting" refer to the transfer of a sample of an analyte protein from an electrophoresis gel matrix to a protein-binding membrane.

The term "acyl" means a radical of the general formula —C(=O)—R, wherein —R is hydrogen, hydrocarbyl, amino or alkoxy. "Examples include for example, acetyl (—C(=O)CH$_3$), propionyl (—C(=O)CH$_2$CH$_3$), benzoyl (—C(=O)C$_6$H$_5$). phenylacetyl (—C(=O)CH$_2$C$_6$H$_5$), carboethoxy (—CO$_2$CH$_2$CH$_3$), and dimethylcarbamoyl (—C(=O)N(CH$_3$)$_2$).

The term "alkyl", by itself or as part of another substituent means, unless otherwise stated, a straight, branched or cyclic chain hydrocarbon radical, including di- and multi-radicals, having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$)alkyl, particularly ethyl, methyl and isopropyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

The compounds of formula I useful in the present invention as staining reagents may take the form of salts. The term "salts", embraces salts commonly used to form alkali metal salts and to form addition salts of free acids or free bases. Suitable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid.

Suitable base addition salts of compounds of formula I include for example, metallic salts made from lithium, calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The staining reagents of formula I may be dissolved in water for use in the methods of the invention. The aqueous solutions of staining reagents of formula I may be neutral or acidic, with neutral solutions being preferred.

To form an acidic solution of compounds of formula I, suitable aqueous acids include aqueous acetic acid and aqueous phosphoric acid. Suitable concentrations of aqueous acetic acid include for example from about 0.1% to about 20% acetic acid in water, preferably from about 5% to about 15% acetic acid in water. Suitable concentrations of aqueous phosphoric acid include for example from about 0.1% to about 10% phosphoric acid in water, preferably from about 2% to about 8% phosphoric acid in water.

The staining reagents of formula I may also be dissolved in solvents comprising mixtures of water and organic solvents. Such mixed solvents may include methanol/water and ethanol/water mixtures. Suitable solvent compositions include for example mixtures of from about 0.01% to about 50% of the organic solvent in water, preferably from about 5% to about 35% of the organic solvent in water.

The staining reagents of formula I may be used in solution in concentrations of from about 0.01% to about 5%, preferably in concentrations of from about 0.1% to about 1%, more preferably, in concentrations of from about 0.1% to about 0.5%. Concentrations of compounds of formula I which are higher or lower than the above values are also contemplated. Suitable concentrations of the staining compounds of the present invention may be reasonably determined by one of skill in the art of protein staining.

The staining methods of this invention may be performed at room temperature. Higher and lower temperatures are also contemplated and particular applications of the methods of the invention may be optimized to temperatures significantly higher or lower than room temperature. For example, analysis of a thermally unstable protein may be performed at a temperature substantially below room temperature.

Generally, when staining a protein-binding membrane containing one or more protein spots bound thereto, the membrane is dipped into an aqueous solution of a compound of formula I at room temperature and incubated for a time sufficient to visualize the protein spots. The time required for staining is typically from about 30 seconds to about ten minutes, preferably from about 30 seconds to about five minutes, more preferably from about 30 seconds to about one minute.

Once the stain has developed sufficiently for visualization of the protein spots, the membrane is removed from the staining reagent and is destained in water by dipping the stained membrane into a reservoir of aqueous liquid, preferably water, preferably at room temperature. The membrane destaining step washes the staining reagent off of the portions of the membrane not bound to protein spots. The destaining step is continued until sufficient stain has washed off that the contrast is optimized between the stained membrane-bound protein and the background of the destained membrane. Such optimization of contrast in the destaining procedure can reasonably be determined by one of skill in the art of protein staining. The staining and destaining times will depend on factors including the composition of the protein-binding membrane, the nature and quantity of the protein analyte and purpose of the analysis, i.e., qualitative detection alone or quantitative analysis. Typically, the destaining step comprises destaining for a time interval of from about one minute to about sixty minutes, preferably from about one minute to about five minutes. Longer and shorter destaining time intervals are also contemplated.

The object of the staining and destaining process is to generate a color change in the protein spots that is visually detectable to the human eye. Those of ordinary skill in the art of protein staining may determine a suitable time interval for the staining and destaining steps which provides visualization of the protein spots.

Figure 1B:
Figure 1C:
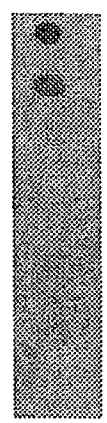
Figure 1D:
Figure 1E:
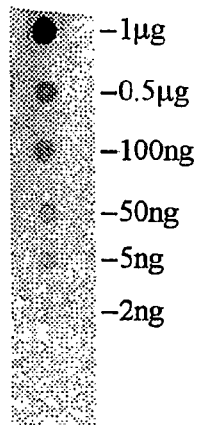
Figure 2A:
FIGS. 2a-2e are photographic reproductions of nitrocellulose membranes spotted with bovine serum albumin at six concentrations from 2 nanograms to 1 microgram and stained with: Ponceau S (FIG. 2a); amido black 10b (FIG. 2b); coomassie blue (FIG. 2c); colloidal gold (FIG. 2d); and reactive brown 10 (FIG. 2e).
Figure 2B:
Figure 2C:
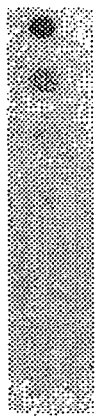
Figure 2D:
Figure 2E:
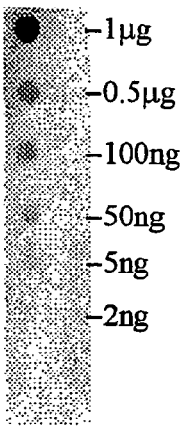

The staining methods of the invention demonstrate substantially the same sensitivity on all protein-binding membranes. This property of equal sensitivity on different membranes is illustrated in FIGS. 1e, 2e and 3e, which show staining with reactive brown 10 of protein spots in a range of concentrations on membranes of three different compositions.

Figure 3A:
FIG. 3a-3e are photographic reproductions of nylon membranes spotted with bovine serum albumin at six concentrations from 2 nanograms to 1 microgram and stained with: Ponceau S (FIG. 3a); amido black 10b (FIG. 3b); coomassie blue (FIG. 3c); colloidal gold (FIG. 3d); and reactive brown 10 (FIG. 3e).
Figure 3B:
Figure 3C:
Figure 3D:
Figure 3E:
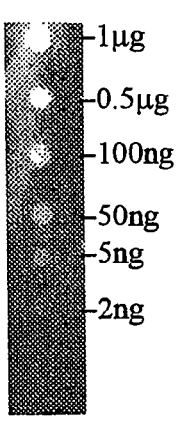

As seen in FIG. 3e, when using nylon membranes, the destaining step gives a reverse staining product wherein the portions of the membrane that are not bound to protein remain darkly stained while the areas of the membrane bound to protein spots are destained. The sensitivity of the method is not diminished by the reverse staining appearance of the destained nylon membrane. Nanogram or picogram quantities of protein bound to a protein-binding membrane may be detected and/or quantified on membranes of various compositions.

The staining reagent may be removed from the stained proteins without denaturing or otherwise degrading them. The proteins retain their tertiary structure, antigenic activity, enzymatic activity, etc. that may be necessary for further characterization of analyte proteins.

Protein staining may be reversed by treating the stained membrane with an aqueous alkaline solution. Suitable aqueous alkaline solutions include solutions of alkali metal hydroxides. The destaining solution concentration may range from about 0.01 to about 1N, though higher and lower concentrations are possible. Particularly preferred is about 0.1N sodium hydroxide.

Protein staining is reversed by immersing the membrane containing stained proteins in a reservoir of the aqueous alkaline solution at room temperature. The incubation time required for removal of the staining reagent from the protein spots may be from about one minute to about ten minutes, preferably from about one minute to about five minutes. The end point of the reversal of the staining method is visual such that the stain removal is complete when the protein spot is no longer detectable visually to the human eye. Determination of the precise time required for reversal of the staining procedure may be readily determined by one of ordinary skill in the art.

The membrane is washed with water following the protein staining reversal step and immersed for one minute or less in a reservoir containing water or a mixed aqueous organic solvents. The mixed aqueous-organic solvent may comprise, for example, from about 1 to about 50% organic solvent, preferably from about 1 to about 35% organic solvent. Such solvents include, for example, water-methanol and water-ethanol.

The staining method of the present invention may be adopted to quantify proteins of interest (hereinafter "protein analyte"). A specific volume of a protein analyte is spotted onto a protein-binding membrane via, for example, a calibrated micropipette.

The protein analyte may be dissolved in an aqueous solution (either neutral, acidic, or basic), or in an aqueous-organic mixed solvent.

A series of solutions of known concentrations of a standard protein is prepared. Each standard solution is spotted on the same membrane with the protein analyte. Bovine serum albumin (BSA) is an example of a protein standard useful in the above quantitative analysis. Preferably the concentrations of the standard protein solution will span a range around the estimated concentration of the analyte protein.

The membrane containing the analyte protein spot and the series of standard protein spots is then stained with a staining reagent of formula I and destained according to methods described herein.

Image quantification of the stained proteins data may be carried out by scanning the stained protein spots with an electronic scanner such as, for example, a Hewlett Packard ScanJet IIcx. An alternative to scanning the spots on the protein-binding membrane is to photograph the membrane with a digital camera or CCD.

Analysis of the scanned or photographed image may be by use of image analysis software such as, for example Image Quant software. Analysis of the image may also use a densitometer such as, for example, a Molecular Dynamics Densitometer or any other analytical methods of quantifying the color density of a spot on a protein-binding membrane.

The image quantification data for spots of the series of known concentrations of the protein standard may be used to generate a standard curve that related the spot density to protein concentration. The analyte protein concentration may be calculated using the image quantification data from the protein analyte spot.

Kits may be assembled that conveniently provide the components for practicing the methods of the invention. A kit for visualizing proteins bound to a protein-binding membrane comprises a supply of protein-binding membranes and a staining reagent comprising at least one compound of formula I.

The supply of protein-binding membranes may include membranes of a single composition for a particular application, or may include a variety of membranes of different compositions to provide a flexible tool for visualizing proteins on different protein-binding membranes.

The staining reagent provided in a kit of the invention may comprise a single compound of formula I or a mixture of compounds of formula I or both. The staining reagent may be preformulated as described herein, or may be supplied with water, aqueous acid or mixed aqueous organic solvent suitable for the practice of the staining methods of the invention and instructions for formulating the staining reagent. The kit may further contain reservoirs suitable for the practice of the staining methods of the invention.

A kit for quantifying small amounts of protein comprises the components of the kit described above for visualizing proteins and further contains a set of one or more solutions of a protein standard of known concentration. Alternately, a stock standard solution may be provided with instructions for preparation of a series of different concentrations. The standard protein solutions may comprise solvents including, for example, water, aqueous acid, aqueous buffer solutions or mixed aqueous organic solvent suitable for maintaining a fixed concentration of the protein standard. The kit may also include reservoirs and calibrated micropipettes for use in the practice of the quantitative analyses of the present invention.

The practice of the invention is illustrated by the following non-limiting examples.

EXAMPLES

Example 1

Comparison of Different Staining Methods

Membranes of three types (PVDF, nitrocellulose, and nylon) were prepared by cutting into strips (1 cm×8 cm). Each of the membrane strips were spotted with 1 µL spots of bovine serum albumin (BSA) in a series of amounts comprising: 2 ng, 5 ng, 50 ng, 100 ng, 500 ng and 1000 ng of protein. Due to the hydrophobic nature of the PVDF membrane, the protein solution for spotting of the PVDF membrane was mixed with an equal volume of caprolactone before spotting.

Each membrane of each composition was then stained with one of a group of five staining compositions selected as follows:

One membrane of each composition was stained using ponceau S. In this procedure, the membrane was incubated in solution with a concentration of 0.1% (w/v) of ponceau S stain in 5% acetic acid for 5 min. The stain was then decanted and the membrane washed with deionized water until the background was removed leaving only the detected protein. The membranes stained using ponceau S are shown in FIGS. 1a, 2a and 3a One membrane of each composition was stained using amido black 10b. In this procedure, the membrane was incubated in a 0.1% (w/v) solution of amido black which was dissolved in 10% (v/v) acetic acid and 30% (v/v) methanol. The membrane was incubated for 30 seconds and the stain removed. The membrane was destained with water until the background was removed satisfactorily. The membranes stained using amido black 10b are shown in FIGS. 1b, 2b and 3b One membrane of each composition was stained using coomassie blue. In this procedure, the membrane was incubated in a 0.125% coomassie blue R-250, 50% methanol and 10% acetic acid solution for 1 hr. The stain was then removed and the membrane destained with 25% methanol until the background was removed. The membranes stained using coomassie blue are shown in FIGS. 1c, 2c and 3c One membrane of each composition was stained using colloidal gold. In this procedure, the membrane was washed three times for 20 min in tris-buffered saline, pH 7.4 containing 0.05% Tween 20 (TTBS), followed by three 2 min washes in deionized water. The formulation of colloidal gold is 5 mL of 1% gold chloride, 6 mL formamide, 5 mL tween 20 and 3 mL of 0.2M potassium hydroxide added dropwise to a total volume of 500 mL. The stain was allowed to stir vigorously overnight and the pH was brought to 3.5 with formic acid. The membrane was then stained to the desired intensity. The membranes stained using colloidal gold are shown in FIGS. 1d, 2d and 3d One membrane of each composition was stained using reactive brown 10, by incubating the membranes with a 0.1% solution of reactive brown 10 in water for approximately one minute. This step was followed by destaining by incubating in water for about one minute. The membranes stained using reactive brown 10 are shown in FIGS. 1e, 2e and 3e.

FIGS. 1a-1e show the sensitivity of all the stain compositions on protein bound to PVDF membrane. It was noted that both coomassie blue and amido black 10b were difficult to destain on PVDF membrane and subsequently high background levels of the stain remained even after extensive washing. The maximum demonstrated sensitivities achieved on PVDF membranes are summarized in Table 1 below.

TABLE 1

Maximum sensitivities of tested stain compositions of PVDF membranes as shown in FIGS. 1a-1e.

| Stain composition | Maximum sensitivity |
|---|---|
| ponceau S | 100 ng |
| amido black 10b | 50 ng |
| coomassie blue | 50 ng |
| colloidal gold | 2 ng |
| reactive brown 10 | 2 ng |

FIGS. 2a-2e show the sensitivity of all the stain compositions on protein bound to nitrocellulose membrane. The maximum demonstrated sensitivities achieved on nitrocellulose membranes are summarized in Table 2 below.

TABLE 2

Maximum sensitivities of tested stain compositions of nitrocellulose membranes as shown in FIGS. 2a-2e.

| Stain composition | Maximum sensitivity |
|---|---|
| ponceau S | 100 ng |
| amido black 10b | 50 ng |
| coomassie blue | 50 ng |
| colloidal gold | 2 ng |
| reactive brown 10 | 2 ng |

FIGS. 3a-3e show the sensitivity of all the stain compositions on protein bound to nylon membrane. None of the stain compositions other than reactive brown 10 were capable of effecting protein detection. Reactive brown yielded a reverse staining appearance as shown in FIG. 3e, but nonetheless gave the same sensitivity on nylon membrane as on the other membrane compositions. The maximum demonstrated sensitivities achieved on nylon membranes are summarized in Table 3 below.

TABLE 3

Maximum sensitivities of tested stain compositions of nylon membranes as shown in FIGS. 3a-3e.

| Stain composition | Maximum sensitivity |
|---|---|
| ponceau S | >1,000 ng |
| amido black 10b | >1,000 ng |
| coomassie blue | >1,000 ng |
| colloidal gold | >1,000 ng |
| reactive brown 10 | 2 ng |

Example 2

Quantitation of Proteins Using Reactive Brown 10

1 µL of an unknown protein solution is spotted on a PVDF membrane. 1 µL of each of a series of standard, known concentration solutions of bovine serum albumin, in a range from 2 ng/µL to 20 ng/µL, were spotted on different locations on the same membrane. All of the protein spots were stained with a 0.1% solution of reactive brown 10 in water for approximately one minute. This step was followed by destaining by incubating in water for about one minute. Following the destaining of the membrane, the protein spot were scanned using a Hewlett Packard ScanJet IIcx. The scanned images were then analyzed using a Molecular Dynamics personal Densitometer.

Figure 4:
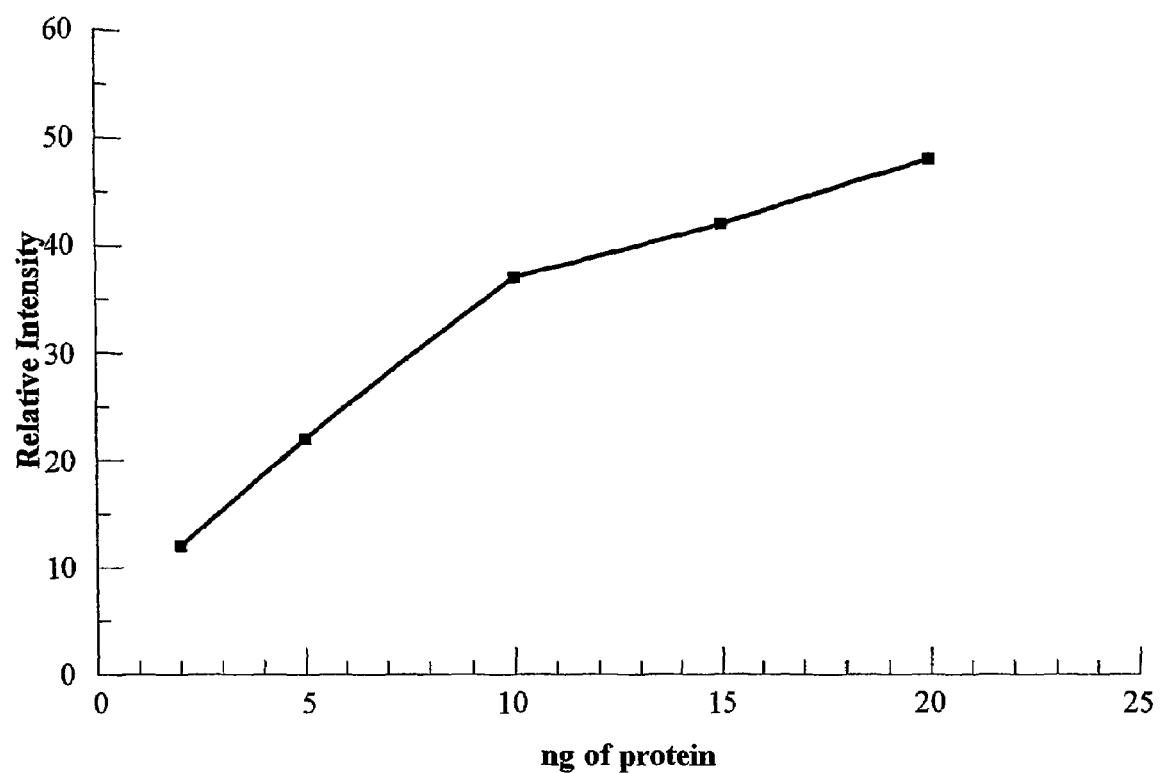
FIG. 4 is a standard curve generated by plotting image quantification data for known concentration protein spots of bovine serum albumin reacted with a solution of reactive brown 10.

A standard calibration curve was generated (FIG. 4) and used to determine the concentration of the unknown protein.

All references cited herein are incorporated by reference. The present invention may be embodied in other specific forms without departing from the spirit of essential attributes thereof and, accordingly, reference should be made to the appended claims, rather than to the foregoing specification, as indication of the scope of the invention.

What is claimed is:

1. A method of quantifying a protein analyte, comprising:
   (1) staining at least one protein analyte spot and a series of protein standard spots of known quantity bound to a protein-binding membrane with a staining reagent comprising reactive brown 10, or a salt thereof
   (2) incubating said protein analyte spot and said protein standard spots bound to the protein-binding membrane with the staining reagent for a time interval sufficient to allow reaction of the protein spot and said protein standard spots with the staining reagent;
   (3) destaining the staining reagent from the protein-binding membrane;
   (4) generating image quantification data for the known protein standard spots and for the protein analyte spot;
   (5) constructing a standard calibration curve using the known concentrations of the protein standard and the corresponding image quantification data; and
   (6) calculating a concentration for the protein analyte.

2. The method of claim 1, wherein the protein-binding membrane is selected from the group consisting of nitrocellulose, nylon and polyvinylidene difluoride.

3. The method of claim 1 wherein the protein standard is bovine serum albumin.

4. A kit for quantifying an amount of a protein, comprising, independently packaged within a single container:
   (1) one or more protein-binding membranes;
   (2) a staining reagent consisting essentially of reactive brown 10, or a salt thereof; and
   (3) a set of one or more solutions of a protein standard of known concentration.

* * * * *